United States Patent [19]

Durrwachter et al.

[11] Patent Number: 5,602,285

[45] Date of Patent: Feb. 11, 1997

[54] PROCESS FOR PREPARING PHENETHANOL ETHERS

[75] Inventors: John R. Durrwachter; Humberto Ramos, Jr.; Mohammad Aslam, all of Corpus Christi, Tex.

[73] Assignee: Hoechst Celanese Corp., Somerville, N.J.

[21] Appl. No.: 363,508

[22] Filed: Dec. 23, 1994

Related U.S. Application Data

[63] Continuation-in-part of Ser. No. 83,951, Jun. 24, 1993, abandoned.

[51] Int. Cl.$^6$ ................................................. C07C 41/00
[52] U.S. Cl. ............................................................ 568/626
[58] Field of Search .................................................. 568/626

[56] References Cited

U.S. PATENT DOCUMENTS 4,328,206  5/1982  Sprecker et al. .................. 424/84

OTHER PUBLICATIONS

Pratt et al JACS 78, pp. 76–78 (1956).
De Jonge et al, Rec. Trav. Chim. pp. 1448–1452 (1955).
Ipatieff, JACS 63 pp. 969–971 (1941).

*Primary Examiner*—Paul J. Killos
*Attorney, Agent, or Firm*—James L. McGinnis

[57] ABSTRACT

Substituted phenethanol ethers are prepared in useful yields by the etherification of corresponding substituted phenethyl alcohols with aliphatic primary alcohols. The etherification is carried out by reacting a substituted phenethyl alcohol with an aliphatic primary alcohol in the presence of an acid catalyst at a temperature of at least about 75° C.

15 Claims, No Drawings

PROCESS FOR PREPARING PHENETHANOL ETHERS

This is a continuation-in-part of application(s) Ser. No. 08/083,951 filed on Jun. 24, 1993, abandoned.

TECHNICAL FIELD OF THE INVENTION

The present invention relates to substituted phenethanol ethers and, more particularly, to a process for the preparation thereof. Still more particularly, the present invention discloses a process for preparing substituted phenethanol ethers (SPEE) by the etherification of corresponding substituted phenethyl alcohols.

BACKGROUND OF THE INVENTION

The compound 4(2'-methoxyethyl)phenol (MEP), a substituted phenethanol ether prepared in accordance with the present invention, is a known compound. It is used as an intermediate in the production of 1-[4-(2-methoxyethyl)phenoxy]-3-[1-(1methoxyethyl)amino]-2-propanol, a beta-adrenergic blocker known as metoprolol tartrate and described in 2 Pharmaceutical Manufacturing Encyclopedia, 100–1010 (2nd ed. 1988).

Several methods have been employed in the past to manufacture 4-(2'-methoxyethyl) phenol (MEP). A method is described in Baird et al., Neighboring Carbon and Hydrogen. LI.[1]. Dienones from Ar, O-3 Participation. Isolation and Behavior of Spiro (2,5)octa-1,4-diene-3-one, 85 Am. Chem. Soc'y 567, 575 (1963) and in Communication to the Editor from Baird et al., 79 Am. Chem. Soc'y 756–757 (1957). In that method, 4-(2'-methoxyethyl)phenol is synthesized from phenylacetic acid through a multi-step process.

French Patent 2,487,338 discloses the preparation of 4-(2'-methoxyethyl)- phenol utilizing brominated alkoxyphenol as a starting material. The method utilizes a multi-step process which includes a technically difficult Grignard reaction.

Belgian patent 885,030 discloses another method for the preparation of 4-(2'-methoxyethyl)phenol. In that method, the starting material is 4-hydroxystyrene. Several steps are used to obtain the final product.

Still another method for the production of 4-(2'-methoxyethyl)phenol is disclosed in Hallberg et al., A New Route to 4-(2'-methoxyethyl)phenol via Palladium-Catalyzed Arylation of Methyl Vinyl Ether, 15(13) Synthetic Com., 1131–6 (1985) wherein 4-(2'-methoxyethyl)phenol is prepared via palladium-catalyzed arylation of methyl vinyl ether. The palladium catalyzed reaction of methyl vinyl ether with 4-bromonitrobenzene, followed by hydrogenation and subsequent diazotization forms 4-(2'-methoxyethyl)phenol.

In U.S. Pat. No. 5,107,034, there is described a process for preparing MEP by brominating 4-hydroxyacetophenone to produce alpha-bromo-5-hydroxy-acetophenone, and then causing a methoxide-bromide exchange to thereby produce alpha-methoxy-4-hydroxyacetophenone; and then conducting a single step reduction of alpha-methoxy-4-hydroxyacetophenone with at least two (2) equivalents of hydrogen per equivalent of alpha-methoxy-4-hydroxyacetophenone in the presence of a hydrogenation catalyst to thereby directly produce MEP.

In U.S. Pat. No. 5,124,489, there is disclosed a process for preparing substituted phenethanol ethers by the catalytic reduction of corresponding substituted phenylglyoxal acetals.

The above prior art references are disclosed in accordance with the terms of 37 CFR 1.56, 1.97, and 1.98. All of these references are incorporated herein by reference in their entirety.

One of the disadvantages of the above-referenced processes is that they include several, often complex, steps which give rise to economical and ecological problems. Furthermore, another disadvantage of some of the above-referenced processes is that they utilize expensive starting materials.

According to the present invention, a simple economical method is disclosed wherein 4-hydroxyphenethyl alcohol, a commercially available material, is subjected to etherification to prepare 4-(2'-methoxyethyl)phenol (MEP). The method is also employed to prepare other substituted phenethanol ethers which are believed to be useful as intermediates in pharmaceutical products by the etherification of corresponding substituted phenethyl alcohols.

These and other advantages and objects of the present invention will become apparent from the following description.

SUMMARY OF THE INVENTION

Substituted phenethanol ethers are produced by the etherification of the corresponding substituted phenethyl alcohols. According to the present invention, a phenethyl alcohol reacts with an aliphatic primary alcohol in the presence of an acid catalyst to prepare the corresponding phenethanol ether in useful yield. The method is used for the production of a variety of substituted phenethanol ethers including, but not limited to, 4-(2'-methoxyethyl)phenol, 4-(2'-n-propoxyethyl)phenol, and 4-[2'-3"- methyl- butoxy)ethyl]phenol. The acid catalyst is selected from the group consisting of protic acids and Lewis acids.

The reaction is preferably carried out in an enclosed reactor with the pressure of the reactor being about 100 psig to about 1000 psig and at a temperature in the range of about 100° C. to about 150° C. for about 0.5 to about twenty-four (24) hours. Upon completion of the reaction, the reaction mass may be treated by well-known separation techniques to recover the product and the acid catalyst.

DETAILED DESCRIPTION OF THE INVENTION

According to the present invention, a substituted phenethanol ether is prepared in useful yield by the etherification of a corresponding substituted phenethyl alcohol and, more particularly, by the reaction of such phenethyl alcohol with an aliphatic primary alcohol in the presence of a suitable acid catalyst. The substituted phenethanol ethers prepared in accordance with the present invention are of the formula:

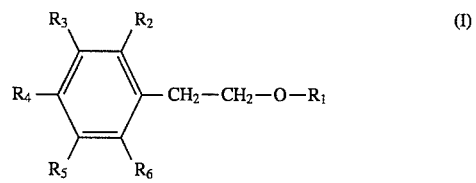

which is hereinafter referred to as Formula I. The corresponding reactant substituted phenethyl alcohol is of the formula:

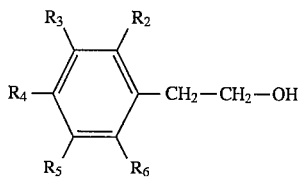

(II)

which is hereinafter referred to as Formula II.

In Formulas I and II, $R_1$ is a primary alkyl group containing preferably one (1) to twenty (20) carbon atoms and most preferably, one (1) to six (6) carbon atoms. Furthermore, in Formulas I and II, $R_2$, $R_3$, $R_4$, $R_5$, and $R_6$, are independently hydrogen, an alkyl group, a substituted or an unsubstituted aryl group, a hydroxy group, an alkoxy group, a substituted or an unsubstituted aryloxy group, a halogen, an acyl group, an aroyl group, an alkyl group terminated with a carboxylic acid or acid derivative group (e.g. an ester or amide), an acyloxy group, an aroyloxy group, an amino group, an alkyl substituted amino group, an amino group substituted with a substituted or an unsubstituted aryl group, a nitrile group or a nitro group. When $R_2$, $R_3$, $R_4$, $R_5$, or $R_6$ is an alkyl group, said group contains preferably one (1) to twenty (20) carbon atoms and, most preferably one (1) to six (6) carbon atoms. When $R_2$, $R_3$, $R_4$, $R_5$, or $R_6$, is a substituted or unsubstituted aryl group, a substituted or unsubstituted aroyl, aroyloxy or aryloxy group, or an amino group substituted with a substituted or unsubstituted aryl group, the aryl group thereof is preferably a phenyl group. Substituents on the substituted aryl groups include but are not limited to alkyl, phenyl, halogens, fluoroalkyl, nitro, nitrile, acyl, alkoxy, acyloxy, aryloxy, aroyl, and aroyloxy. It should be understood that, unless stated otherwise, the above definitions of $R_1$, $R_2$, $R_3$, $R_4$, $R_5$, and $R_6$ shall be applicable hereinafter.

In accordance with the present invention, the etherification step or reaction to prepare the phenethanol ethers of Formula I from the corresponding phenethyl alcohol of Formula II is represented stoichiometrically as follows (Reaction 1):

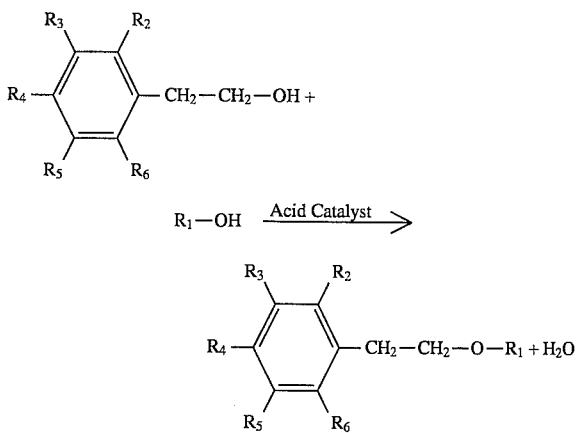

Examples of substituted phenethanol ethers prepared in accordance with the present reaction include, but are not limited to, 4-(2'-methoxyethyl)phenol (Formula III); 4-(2'-n-propoxyethyl)phenol (Formula IV); and 4-[2'-(3"-methylbutoxy)ethyl]phenol (Formula V). These compounds are shown below:

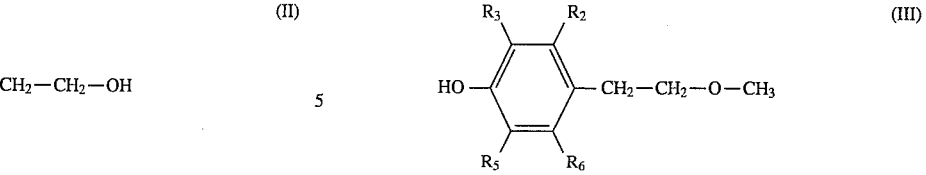

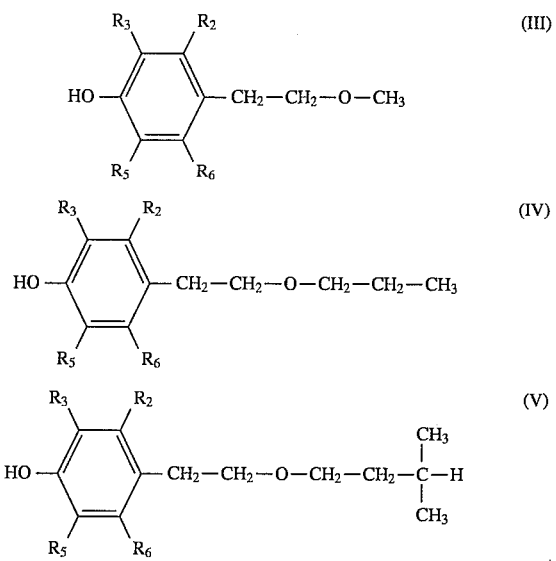

It is believed that the acid catalyst promotes the conversion of the

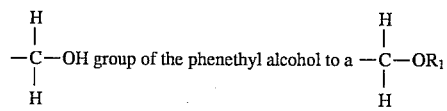

group. It is totally unexpected to achieve the production of a specific ether compound in useful yields when reacting two primary alcohols together. A useful yield of the phenethyl ether is generally at least about 10%, preferably is at least about 20%, and most preferably is at least about 50%.

Any suitable acid catalyst that can promote the above etherification step may be used. Acid catalysts which function in the capacity to achieve the desired end result, i.e. the promotion of Reaction I above, am soluble acids and insoluble acids. Typical soluble acids include, without limitation, hydrochloric acid, sulfuric acid, methanesulfonic acid, and p-toluenesulfonic acid. Typical insoluble acids include, without limitation, zeolites and $H^+$ ion exchange resins such as Dowex brand catalysts, Amberlyst brand catalysts, and the like. Insoluble acid catalysts such as sulfonated copolymer of styrene and divinyl benzene (e.g. "Amberlyst 15" manufactured by Rohm & Haas Corporation of Philadelphia, Pa.), or an acid clay such as an activated clay adsorbent such as "Filtrol 105" are suitable materials that can be used. The acid catalysts are either soluble or insoluble in the overall reaction mass. The preferred acid catalyst is one which is insoluble. Of these, zeolites and $H^+$ ion exchange resins are preferred.

When an $H^+$ ion exchange resin is used as a catalyst, some dialkyl ether is obtained as a by-product from the etherification reaction of the alkyl alcohol (e.g. dimethyl ether from methanol). A very small amount of the dimer of the phenethyl alcohol is also obtained when a high concentration of the phenethyl alcohol is used. Finally, small yield of the aromatic alkoxy products resulting from the etherification reaction of the alcohol with the phenolic group of the starting material and product are obtained when a hydroxyphenethanol is used as a starting material. Typically about 0.2% to about 0.4% of the aromatic alkoxy products resulting from the etherification reaction of the alcohol with the phenolic group of the starting material or product are obtained when a hydroxyphenethanol is used as a starting material. Thus, about 0.2% to about 0.4% of the anisole products compared with the desired phenethyl ether are formed from hydroxyphenethanol and methanol.

Acidic zeolites appear to generate little or no aromatic alkoxy by-product from the reaction of the aliphatic alcohol with phenolic groups, and are thus preferred catalysts for hydroxyphenethyl alcohols. Reactions catalyzed by the zeolites are not as fast as those catalyzed by the ion exchange resins, but still typically result in >50% conversion of 4-hydroxyphenethyl alcohol and methanol to 4-(2'-methoxyethyl) phenol after an overnight batch run. Preferred zeolites are selected frown the well-known class of synthetic aluminosilicate zeolites known as ZSM-5 zeolites. These are described in U.S. Pat. No. 3,702,886, which is incorporated herein by reference. These zeolites are used in their acidic form. Preferably, the silica:alumina ratio is in the range of about 10:1 to about 60:1. A silica:alumina ratio of about 38:1 produces excellent results. These zeolites are commercially available. Zeolites in extruded form (e.g. $\frac{1}{16}$ inch extrudate) are more selective than the same zeolites in powder form.

These zeolites catalyze the formation of a small amount of by-product resulting from the alkylation of the aromatic ring by the aliphatic alcohol. Thus, a small amount of 4-(2-methoxyethyl)-2-methylphenol (Formula VI below) is obtained from reaction of methanol and 4-hydroxyphenethyl alcohol using a zeolite catalyst.

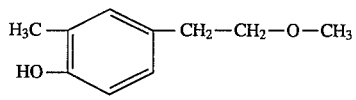

VI

The ring alkylated product is typically obtained at a level of <1% compared with the desired 4-(2'-methoxyethyl) phenol. The amount of ring alkylation can be reduced further by lowering the amount of alcohol and adding water to inhibit the tendency toward ring alkylation. Thus if approximately equimolar amounts of 4-hydroxyphenethyl alcohol and methanol are reacted in the presence of a ZSM-5 type of zeolite and water, the ratio of 4-(2'-methoxyethyl) phenol to ring alkylated by-product is increased to greater than 1000:1. The amount of water generally is in the range of about 5% to about 50% by weight (of the reacting alcohols and water); about 25% by weight of water yields a product in which the ratio of the desired phenethyl ether to ring alkylated impurity is about 1200:1.

Although a small amount of the acid catalyst, e.g. one (1) percent by weight of the total weight of the reaction mass, is sufficient to promote Reaction I of the present invention, it is preferred to use frown about five (5) to about fifty (50) percent by weight; more preferably from about five (5) to about ten (10) percent by weight, based on the total weight of the reaction mass.

While Reaction I above discloses the stoichiometrically balanced equation, it is to be understood that the substituted phenethyl alcohol (SPEA) can be used in an amount of from about five (5) percent to about seventy (70) percent by weight, based on the total weight of the reaction mass. Also, the primary aliphatic alcohol (PAA) can be used in an amount of from about thirty (30) percent to about ninety-five (95) percent by weight, based on the total weight of the reaction mass. PAA includes, but is not limited to, methanol, n-butyl alcohol, and isoamyl alcohol.

In carrying out the reaction, the SPEA, PAA, and the acid catalyst are charged to a corrosion-resistant reactor. The reactor is purged with an inert gas such as nitrogen. The inert gas can also be used to pressurize the reactor during the reaction if desirable. Accordingly, it is desirable to operate the reaction under pressure in order to conduct the reaction in liquid phase. The pressure therein should be at least fifty (50) psig, preferably in the range of about 100 psig to about 1000 psig, and more preferably, in the range of about 100 psig to about 750 psig.

The reaction is carried out at a temperature above 75° C., and preferably in the range of about 100° C. to about 300° C., and most preferably, in the range of about 100° C. to about 150° C. The rate of the reaction depends on the amount of acid catalyst, the pressure, and the reaction temperature.

The best yields are obtained when the amount of SPEA is in the higher portion of the aforesaid ranges, the amount of the catalyst used is within the lower portion of the aforesaid range, and the temperature and the pressure are in the upper portion of the aforesaid ranges. High yields, however, are also observed when the amount of catalyst is in the upper portion of the aforesaid ranges and the amount of SPEA, the reaction temperature and the pressure are in the lower portion of their respective aforesaid ranges.

The reaction mass is continuously stirred by well-known stirring means. The reaction is carried out for a sufficient period of time to obtain a satisfactory conversion of the SPEA to the SPEE product. Depending on the amount of the catalyst, the reaction temperature and the pressure, the time period may be in the range of about 0.50 hours to about twenty-four (24) hours or longer. Preferably, the reaction is carried out for a time period in the range of about one (1) hour to about eighteen (18) hours. The reaction is relatively slow and can be carried out in a batch mode, a semi-batch mode, or a continuous mode.

Upon the completion of the reaction, the SPEE product may be separated from the reaction mass by well-known techniques such as distillation, crystallization, and filtration. For example, the acid catalyst can be recovered by filtration of the reaction mass. The acid catalyst may be reformulated and recirculated to the reactor for further utilization. The unreacted SPEA can be separated from SPEE by distillation or crystallization and recycled.

The following examples further illustrates the invention but are not to be construed as limitations on the scope of the invention contemplated herein.

Example 1

4-(2'-Methoxyethyl)Phenol

A solution of twenty (20) grams 4-hydroxyphenethyl alcohol in 150 ml methanol containing 36.75 grams sulfuric acid (catalyst) were loaded into a 300 cc autoclave. The autoclave was then sealed and purged with nitrogen and pressurized with nitrogen gas to 500 psig. The autoclave was then heated to 100° C. with stirring at 300 rpm. The reaction was allowed to take place for approximately twenty-four (24) hours. The autoclave was then purged with nitrogen, cooled to 5° C., and vented slowly. The resultant material was 90 ml of a dark, greenish-black solution. An aliquot was treated with base and analyzed by gas chromatography (GC). A 40% yield of 4-(2'-methoxyethyl)phenol was obtained.

Example 2

4-(2'-Methoxyethyl)Phenol

A mixture of 20.0 grams 4-hydroxyphenethyl alcohol, 150 ml methanol, and 10.5 grams Zeolite ZS FM-5 catalyst (solid) was loaded into a 300 cc autoclave. The autoclave was then sealed and purged with nitrogen and pressurized with nitrogen gas to 210 psig. The autoclave was then heated up to 125° C. over a four (4) hour period with stirring at 250 rpm. The pressure rose from 210 psig to 400 psig. The reaction was allowed to take place for approximately twelve (12) hours. The autoclave was then purged with nitrogen and cooled to room temperature. The catalyst was filtered off, providing 19.5 grams of a gray solid. A 58% yield of 4-(2'-methoxyethyl)phenol was obtained.

Example 3

4-(2'-Methoxyethyl)Phenol

A mixture of 20.0 grams 4-hydroxyphenethyl alcohol, 100 ml methanol, and 10.0 grams Dowex 50 (H+form) catalyst were loaded into an autoclave. The autoclave was then sealed and purged with nitrogen and pressurized with nitrogen gas to 200 psig. The autoclave was then vented of excess pressure, sealed, and heated to 118° C. over a sixteen (16) hour period with stirring at 300 rpm. The pressure rose from 200 psig to 440 psig. The reaction was allowed to take place for approximately sixteen (16) hours. The autoclave was then purged with nitrogen and cooled to 17.2° C. (230 psig) and then vented. The solid catalyst was filtered off, providing 15.5 grams of oil which solidified. A 31% yield of 4-(2'-methoxy-ethyl)phenol was obtained.

Examples 4–8

The procedure set forth in Example 3 is repeated five (5) separate times but using the substituted phenethyl alcohols shown in Table I where $R_1$, $R_2$, $R_3$, $R_4$, $R_5$, and $R_6$ are defined. The respective ethers are formed with yields ranging from four (4) percent to eighty (80), as follows: Example 4. seven (7) percent; Example 5, about eighty (80) percent; Example 6, ten (10) percent; Example 7, four (4) percent; Example 8, fourteen (14) percent.

TABLE I

| Example | $R_1$ | $R_2$ | $R_3$ | $R_4$ | $R_5$ | $R_6$ |
|---|---|---|---|---|---|---|
| 4 | $CH_3$ | $CH_3$ | H | H | H | H |
| 5 | $CH_3$ | H | H | $CH_3O$ | H | H |
| 6 | $CH_3$ | H | H | Cl | H | H |
| 7 | $CH_3$ | H | H | $NO_2$ | H | H |
| 8 | $CH_3$ | H | H | H | H | H |

Example 9

4-(2'Methoxyethyl)Phenol

A mixture of 80 grams of 4-hydroxyphenethyl alcohol (0.58 moles), methanol (100 ml), and 10 grams of Dowex 50 catalyst ($H^{30}$ form, washed with methanol) was charged into a 300 cc autoclave. The autoclave was sealed, purged with nitrogen and then pressurized under nitrogen. The autoclave was heated to 150° C. overnight with stirring (about 16 hours). The reactor was then cooled, depressurized, and purged with nitrogen to remove by-product dimethyl ether.

The catalyst was filtered off and a few drops of saturated aqueous sodium bicarbonate solution were added to neutralize acidity. The solvent was removed on a rotary evaporator. The product was isolated in 65% yield by distillation, with 33% of the 4-hydroxyphenethyl alcohol remaining unreacted.

Example 10

4-(2'-Methoxyethyl)Phenol

4-Hydroxyphenethyl alcohol (20 grams, 0.145 moles), 10 grams of a ZSM-5 Zeolite catalyst (UOP MFI-38), and methanol (100 ml) are charged to a 300 cc autoclave. The reactor is purged with nitrogen and is then heated with stirring to 150° C. for 15–20 hours. The pressure maximizes at about 350 psig. The reactor is then cooled, vented and degassed with nitrogen to remove by-product dimethyl ether. The catalyst is filtered and the methanol is removed on a rotary evaporator. The product is isolated by distillation. Conversions are typically 50–60% using this procedure and catalyst. By-product 4-(2-methoxyethyl)-2-methylphenol is produced at a level of about 0.5% to about 1% compared with 4-(2'-methoxyethyl) phenol.

Example 11

4-(2'-Methoxyethyl) Phenol

A mixture of 4-hydroxyphenethyl alcohol (60 grams, 0.435 moles), methanol (18 ml), water (26 ml), and a ZSM-5 Zeolite (UOP MFI-38 or MFI-34, 10 grams) are charged to a 300 cc autoclave. The alcohols and water are not a homogenous solution at room temperature. The reactor is charged with 200 psig of nitrogen and is then heated with stirring to 150° C. for 17 hours. Pressure maximizes at about 350 psig. The reactor is then cooled and vented. The product is then purged with nitrogen and filtered. The methanol is removed on a rotary evaporator. The product is isolated by distillation. The conversion to 4-(2'-methoxyethyl) phenol is about 50%. The ratio of product to 4-(2-methoxyethyl)-2-methylphenol is about 1200:1.

While the invention is described with respect to specific embodiments, modifications thereof can be made by one skilled in the art without departing from the spirit of the invention. The details of said embodiments are not to be construed as a limitation except to the extent indicated in the following claims.

What is claimed is:

1. A method of preparing a phenethanol ether of the formula:

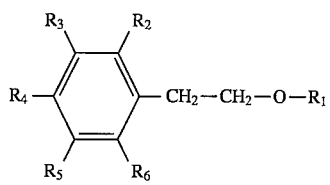

comprising the etherification step of reacting a phenethyl alcohol of the formula:

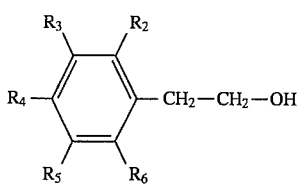

with an aliphatic primary alcohol having the formula $R_1OH$ in the presence of an acid catalyst in an enclosed reactor at a temperature in the range of about 100° C. to about 150° C. to generate the phenethanol ether in a yield of at least about 50%, wherein $R_1$ is a primary alkyl group, $R_2$, $R_3$, $R_5$, and $R_6$ are independently hydrogen, an alkyl group, an unsubstituted or a substituted aryl group, a hydroxy group, an alkoxy group, an unsubstituted or a substituted aryloxy group, a halogen, an acyl group, an aroyl group, an alkyl group terminated with a carboxylic acid or acid derivative group, an acyloxy group, an aroyloxy group, an amino group, an alkyl substituted amino group, an amino group substituted with one or more substituted or unsubstituted aryl groups, a nitrile group or a nitro group, and $R_4$ is hydroxy or methoxy.

2. The method according to claim 1 wherein said acid catalyst is selected from the group consisting of soluble acids and insoluble acids.

3. The method according to claim 1 wherein said acid catalyst is a soluble acid catalyst.

4. The method according to claim 1 wherein said acid catalyst is an insoluble acid.

5. The method according to claim 1 wherein $R_1$ is a methyl, an n-propyl, or an isoamyl group, $R_4$ is a hydroxy group, and $R_2$, $R_3$, $R_5$, and $R_6$ are hydrogen.

6. The method according to claim 1 wherein said etherification step is carried out at a pressure in the range of about 100 psig to about 1000 psig.

7. The method according to claim 1 wherein $R_1$ is methyl, $R_4$ is a hydroxy group, and $R_2$, $R_3$, $R_5$, and $R_6$ are hydrogen.

8. The method according to claim 7 wherein said acid catalyst is an $H^+$ ion exchange resin.

9. The method according to claim 7 wherein said etherification step is carried out at a temperature in the range of about 100° C. to about 150° C. and at a pressure of about 100 psig to about 1000 psig.

10. The method according to claim 7 wherein said aliphatic primary alcohol is methanol and said acid catalyst is sulfuric acid.

11. The method according to claim 10, wherein said phenethyl alcohol is present in an amount of from about five (5) percent to about seventy (70) percent by weight, based on the total weight of the reaction mass, and said methanol is present in an amount of from about thirty (30) percent to about ninety-five (95) percent by weight, based on the total weight of the reaction mass.

12. The method according to claim 7, wherein said acid catalyst is a ZSM-5 zeolite.

13. The method according to claim 12, wherein said zeolite has a silica:alumina ratio in the range of about 10:1 to about 60:1.

14. The method according to claim 12, wherein said etherification step is carried out in the presence of water.

15. The method according to claim 14, wherein said aliphatic primary alcohol is methanol; wherein said water is present in an amount of about 5% to about 50% by weight of the combined amounts of methanol, phenethyl alcohol and water; and wherein said methanol and said phenethyl alcohol are present in approximately equimolar amounts.

* * * * *